(12) United States Patent
Brusselaars et al.

(10) Patent No.: US 8,293,476 B2
(45) Date of Patent: Oct. 23, 2012

(54) METHOD FOR TREATING A SOLUTION IN ORDER TO DESTROY ANY RIBONUCLEIC ACID AFTER AMPLIFICATION

(75) Inventors: Wilco Brusselaars, Lieshout (NL); Fokke Venema, Hilversum (NL)

(73) Assignee: Biomerieux, Marcy l'Etoile (FR)

( * ) Notice: Subject to any disclaimer, the term of this patent is extended or adjusted under 35 U.S.C. 154(b) by 170 days.

(21) Appl. No.: 12/733,936

(22) PCT Filed: Dec. 11, 2008

(86) PCT No.: PCT/EP2008/010519
§ 371 (c)(1),
(2), (4) Date: Mar. 30, 2010

(87) PCT Pub. No.: WO2009/074315
PCT Pub. Date: Jun. 18, 2009

(65) Prior Publication Data
US 2010/0233713 A1    Sep. 16, 2010

(30) Foreign Application Priority Data
Dec. 12, 2007 (EP) ................... 07024024

(51) Int. Cl.
*C12Q 1/68* (2006.01)
*C12P 19/34* (2006.01)
(52) U.S. Cl. .............. 435/6.12; 435/6.1; 435/6.11
(58) Field of Classification Search .............. None
See application file for complete search history.

(56) References Cited

U.S. PATENT DOCUMENTS

| 5,418,149 A | 5/1995 | Gelfand et al. |
| 5,965,399 A | 10/1999 | Chatterjee et al. |
| 2002/0034804 A1* | 3/2002 | Iwamoto et al. ............. 435/184 |
| 2002/0172972 A1 | 11/2002 | Tabor et al. |
| 2006/0051771 A1 | 3/2006 | Murphy et al. |

FOREIGN PATENT DOCUMENTS

| WO | WO 99/07887 A2 | 2/1999 |
| WO | WO 02/070735 A2 | 9/2002 |
| WO | WO 2004/094674 A1 | 11/2004 |
| WO | WO 2005/089929 A2 | 9/2005 |

OTHER PUBLICATIONS

Raines, "Ribonuclease A," *Chem. Rev.*, vol. 98, 1998, pp. 1045-1065.
Blackburn et al., "Ribonuclease Inhibitor from Human Placenta," *The Journal of Biological Chemistry*, vol. 252, No. 16, 1977, pp. 5904-5910.
Leone et al., "Molecular beacon probes combined with amplification by NASBA enable homogeneous, real-time detection of RNA," *Nucleic Acids Research*, vol. 26, No. 9, 1998, pp. 2150-2155.
International Search Report issued for International Application No. PCT/EP2008/010519 on Sep. 22, 2009.

\* cited by examiner

*Primary Examiner* — Young J Kim
(74) *Attorney, Agent, or Firm* — Oliff & Berridge, PLC

(57) ABSTRACT

The present invention provides a method for treating a solution containing among others, target nucleic acid to be amplified in order to destroy any ribonucleic acid that is present in the solution and that could possibly be amplified in another assay. The method is useful to avoid carry-over contamination between experiments.

Thus, the present invention provides a method for treating a solution containing at least one target nucleic acid of interest to be amplified comprising the following steps:
  contacting suitable amplification reagents and at least one target nucleic acid in the presence of
    i. at least one ribonuclease (RNase), and
    ii. one ribonuclease inhibitor,
  the RNase being inhibited by the ribonuclease inhibitor; amplification reagents, RNase, ribonuclease inhibitor and target nucleic acid form the solution;
  performing a transcription-based amplification of the target;
  treating said solution in order to inactivate the ribonuclease inhibitor and activate the RNase;
  degrading any RNA that is present in the solution by the action of said RNase.

The present invention is especially useful in methods for diagnostic, preventive and therapeutic applications.

27 Claims, 5 Drawing Sheets

METHOD FOR TREATING A SOLUTION IN ORDER TO DESTROY ANY RIBONUCLEIC ACID AFTER AMPLIFICATION

The present invention provides a method for treating a solution containing among others, target nucleic acid to be amplified in order to destroy any ribonucleic acid that is present in the solution and that could possibly be amplified in another assay. The method is useful to avoid carry-over contamination between experiments.

The development of the molecular biology allows the sensitive detection of nucleic acids by using amplification technologies. The amplification methods have become very powerful tools, since they allow the exponential amplification of very small quantities of nucleic acids in a relatively short time. This generated very powerful assays with sensitivities down to single copies of RNA or DNA. Due to this high sensitivity, a major inconvenience of using these techniques lies in the unwanted amplification of nucleic acid sequences from previous amplification reactions, leading to erroneous results (false positives) in clinical tests. This phenomenon wherein amplicons from an earlier amplification are detected in other new samples, is called: contamination.

A primary source of contamination is target sequences carried-over from previous amplifications, which become dispersed in the laboratory area and serve unintentionally as templates in subsequent amplifications.

Over the years, some general physical precautions have been established like separation of laboratory areas where nucleic acids are isolated and areas where nucleic acids are amplified. Nevertheless, these measures regarding laboratory organisations do not completely prevent contamination.

Thus, besides these general laboratory precautions, a number of pre- and post-amplification methods have been developed to prevent carry-over contamination.

A common pre-amplification method to avoid carry-over in PCR is described in U.S. Pat. No. 5,418,149. It consists in replacing deoxythymidine triphosphate (dTTP) in the amplification reaction by deoxyuridine triphosphate (dUTP). Before a subsequent amplification is carried out, the sample together with the reagents used are subjected to a pretreatment by Uracil-N-glycosilase (UNG). This enzyme cleaves the uracil bases from DNA and so an abasic site originates in the uracil-containing DNA. These abasic sites are susceptible to hydrolysis by heat or alkali, a process that fragments the uracil-containing DNA and renders it unamplifiable in subsequent PCR.

Another pre-amplification method of decontamination is disclosed in the patent application WO-A-99/07887 where a thermolabile DNase is used to degrade carried-over non-target double-stranded DNA present in the amplification reaction mixture. The nucleic acid sample to be amplified can be present in the reaction vessel during the decontamination process, if double stranded DNA sample were denatured e.g. by boiling to render it single stranded and therefore not susceptible to DNase degradation.

The patent application US-A-2002/0172972 discloses a method of digesting nucleic acids contaminating a sample, before amplification, by using an enzyme. This enzyme can be activated by an activator and inactivated by an agent capable of binding to or displacing the activator from the enzyme. In a preferred embodiment, the enzyme, a micrococcal nuclease, is activated by calcium ions in order to remove contaminating nucleic acids from a PCR mixture. Further, EGTA or EDTA is added to remove the bound activator and consequently to inactivate the nuclease. The amplification is then carried out.

Additionally, several more specific methods have been described to eliminate carry-over DNA target products after amplification reaction. These methods include ultraviolet irradiation, gamma irradiation, psoralen treatment. These treatments allow a laboured implementation and have a limited efficiency.

Thus, there is still a demand for a method which can simply and efficiently prevent carry-over in nucleic acid amplification reactions.

In order to satisfy this demand, the present invention provides a method for treating a solution containing at least one target nucleic acid of interest to be amplified comprising the following steps:

contacting suitable amplification reagents and at least one target nucleic acid in the presence of
  i. at least one ribonuclease enzyme (RNase), and
  ii. at least one ribonuclease inhibitor,
the RNase being inhibited by the ribonuclease inhibitor;
  amplification reagents, RNase, ribonuclease inhibitor and target nucleic acid form the solution;
  performing a transcription-based amplification of the target;
  treating said solution in order to inactivate the ribonuclease inhibitor and activate the RNase;
  degrading any RNA that is present in the solution by the action of said RNase.

It is a particular advantage of the present invention that the degradation step can take place without any addition, after the amplification, of any agents capable of degrading nucleic acids. So, according to an advantageously embodiment, the treatment is performed in a reaction vessel and wherein before performing the amplification step, the reaction vessel is closed.

According to the present invention, RNase is inactive before and during the amplification step due to the presence of its inhibitor. Then, after amplification, the solution is treated in order to inactivate the ribonuclease inhibitor and activate the RNase. This treatment can be any treatment which can inactivate ribonuclease inhibitor, for example, heat inactivation or heat treatment.

The RNases are well-known in the art, such as those disclosed in Raines et al., Chem. Rev., 98, 1045-1065 (1998). They are proteins which cleave single stranded RNA. Although RNA in a RNA:RNA or RNA:DNA duplex is not its preferential substrate, RNAse may break it down. Suitable RNases for the present invention include RNase A, RNase B and/or RNase C. Thus, the RNase degrades any RNA present in the solution after amplification of the targets. The degradation is in such a way that the remaining RNAs can not be amplified and therefore do not lead to contamination. The decontamination is any process that cleaves nucleic acids (target or amplicons) at least once within the sequence of said target or corresponding to said target, between the regions where the forward and reverse primers can hybridize. Preferably the number of cleavages of the nucleic acids between the two extremities of the primer set is sufficient to prevent any amplification, such as PCR, NASBA, TMA, 3SR etc. Preferably these cleavages lead to oligonucleotide fragments of less than 100 nucleotides in length, preferentially less than 70, more preferentially less than 50 and even more preferentially less than 30 nucleotides in length.

The ribonuclease inhibitors are also well described in literature, for example, Blackburn et al., the Journal of Biological Chemistry, 252, 16, 5904-5910 (1977) or U.S. Pat. No. 5,965,399. Preferably, the ribonuclease inhibitor is a protein such as placental ribonuclease inhibitor or porcine ribonuclease inhibitor (PRI). According to the present invention, the ribonuclease inhibitor inhibits the said RNase present in the solution but not the enzymes suitable for amplification. Concerning the quantities needed, as ribonuclease activity varies per batch, no concrete amounts of ribonuclease and ribonuclease inhibitor can be given, but, a person skilled in the art will be able to determine them easily. According to the present invention the amount of ribonuclease inhibitor is such that RNase activity is inhibited in the solution. The "RNase activity is inhibited" means that almost the whole, preferably the whole RNase activity is inhibited in the solution before and during the amplification. Furthermore, the "whole RNase activity is inhibited" means that the outcome of the assay is not influenced as compared to an assay that does not contain RNase A and ribonuclease inhibitor.

According to one embodiment of the method, the RNase and ribonuclease inhibitor are mixed before they are brought into contact with suitable amplification reagents and at least one target nucleic acid.

According to the present invention, a transcription-based amplification of the target nucleic acid is performed. The target nucleic acid is DNA or RNA, in the form of double-stranded nucleic acid or single-stranded nucleic acid or a heteroduplex DNA:RNA. In the case where the target is double stranded, the nucleic acids can be melt in order to render them single stranded. In the case where the target is in form of an heteroduplex, it may be possible to use RNAse H, which cleaves the RNA in an RNA:DNA duplex, to break down the RNA and leave single stranded DNA.

In a particular embodiment of the method, the amplification reaction is a NASBA reaction. The NASBA process is described in European patent no. EP-B-0,329,822. Although this process allows amplification of RNA it can be used to amplify double stranded nucleic acid as described in the European patent application EP-A-1,366,179. A major advantage of these methods over PCR is that they are performed isothermally.

According to one embodiment of the method, after having performed the transcription-based amplification, a detection step is performed. In another embodiment, the detection step is performed during the transcription-based amplification. According to these both embodiments, the amplification reagents contain at least one probe to enable the detection step. According to a preferred embodiment of the method, the amplification reagents contain at least one real-time detection probe to enable the detection step. Advantageously, the amplification reagents contain at least one probe which is a molecular beacon.

According to the present invention, a heating step is included. Advantageously, the heating step occurs between 30° C. and 100° C., preferably between 37° C. and 70° C. and more preferably between 60° C. and 65° C.

According to particular embodiments, the heating step can be a one step process, a two step process or a cyclic process. The main goal of the heating step is to inactivate ribonuclease inhibitor and the second goal is to reach a more optimal temperature for ribonuclease to break down the RNA. A third goal of the heating step is to render RNA single stranded. According to one embodiment the heating step is a one step process where the temperature is high enough to inactivate the ribonuclease inhibitor and activate the RNase.

According to another embodiment, the heating step is a two steps process:
 a first heating step where the temperature is higher than the second step to inactivate the ribonuclease inhibitor and activate the RNase;
 a second heating step where the temperature is lower than the first step in order to break down the RNA.

According to this last embodiment, the temperature of the first heating step is between 60° C. and 75° C. In a particular embodiment, this first heating step allows to inactivate ribonuclease inhibitor. In another embodiment, this first heating step allows to inactivate ribonuclease inhibitor and simultaneously stops the amplification because the enzymes of the amplification reaction are heat labile. When an amplification reaction is performed, the progress of the reaction can be monitored by measuring the fluorescence of the probes. The increase of the signal stops when all probes are bound to their target. Nevertheless, this does not mean that no RNA is formed anymore and so it could be useful to stop RNA amplification in parallel with the inactivation of ribonuclease inhibitor.

Again in relation with the two-step process, the temperature of the second heating step is between 30° C. and 70° C.

In a particular embodiment, the temperature of the first heating step allows to inactivate the ribonuclease inhibitor, to activate the RNase and to denature RNA polymerase and reverse transcriptase. The temperature of the second heating step is used to break down the single stranded RNA and the RNA in an RNA:DNA duplex by respectively RNase A and RNase H.

In another embodiment, the heating step is a cyclic process. In a particular embodiment, the cyclic process consists of a heating step to render RNA single stranded and a heating step to degrade RNA. Again in a particular embodiment, the cyclic process takes place after inactivation of the ribonuclease inhibitor.

Another object of the present invention is a kit for carrying out the method comprising:
 suitable amplification reagents including at least one set of primers and at least one probe;
 RNase and ribonuclease inhibitor.

In a particular embodiment, the probe is a real-time detection probe.

In another particular embodiment of the kit, the suitable amplification reagents include nucleotides and amplification enzymes. A kit, adapted for use with NASBA, for example may contain suitable amounts of reverse transcriptase, RNase H and T7 RNA polymerase. Said enzymes may be present in the kit in a buffered solution but can likewise be provided as a lyophilized composition, for example, a lyophilized spherical particle. Such lyophilized particles have been disclosed in PCT/EP95/01268. The kit may further be furnished with buffer compositions, suitable for carrying out an amplification reaction. Said buffers may be optimized for the particular amplification technique for which the kit is intended as well as for use with the particular oligonucleotides that are provided with the kit. In transcription-based amplification techniques, such as NASBA, said buffers might contain, for example, DMSO, which enhances the amplification reaction (as is disclosed in PCT/US90/04733). Furthermore the kit may be provided with an internal control as a check on the amplification procedure and to prevent the occurrence of false negative test results due to failures in the amplification procedure. The use of internal controls in transcription based amplification techniques is described in PCT/EP93/02248. Kits may also contain reagents for the isolation of nucleic acid from biological specimens prior to amplification. A suitable method for the isolation of nucleic acid is disclosed in EP-A-0,389,063.

Definitions

According to the present invention, the term "nucleic acid" (NA) means both DNA and RNA, both in any possible configuration, i.e. in the form of double-stranded (ds) nucleic acid, or in the form of single-stranded (ss) nucleic acid, or as a combination thereof. Such nucleic acid corresponds to a succession of at least two deoxyribonucleotides or ribonucleotides optionally comprising at least one modified nucleotide.

This polynucleotide may also be modified at the level of the internucleotide bond, such as, for example, phosphorothioates, H-phosphonates, alkyl phosphonates, at the level of the backbone such as, for example, alpha-oligonucleotides (FR-A-2 607 507) or PNAs (M. Egholm et al., J. Am. Chem. Soc., 114, 1895-1897, 1992) or 2'-O-alkylriboses. Each of these modifications may be taken in combination as long as at least one phosphate is present in the nucleic acid.

The nucleic acid may be natural or synthetic, an oligonucleotide, a polynucleotide, a nucleic acid fragment, a ribosomal RNA, a messenger RNA, a transfer RNA, a nucleic acid obtained by an enzymatic amplification technique such as:

PCR (Polymerase Chain Reaction), described in U.S. Pat. No. 4,683,195, U.S. Pat. No. 4,683,202 and U.S. Pat. No. 4,800,159, and its RT-PCR (Reverse Transcription PCR) derivative, in particular in a one-step format as described in patent EP-B-0,569,272, RCR (Repair Chain Reaction), described in patent application WO-A-90/01069, 3SR (Self Sustained Sequence Replication) with patent application WO-A-90/06995, NASBA (Nucleic Acid Sequence-Based Amplification) with patent application WO-A-91/02818, and TMA (Transcription Mediated Amplification) with U.S. Pat. No. 5,399,491.

Such "nucleic acid" may be used as target, primer or probe.

The "target sequence" is defined as the part of the nucleic acid molecule to be detected. It is amplified by means of the primers and the amplification related enzymes. The amplification leads to formation of "amplicons", which are the nucleic acid molecules that are physically detected by hybridisation to the probe. Its length is up to 30 nucleotides and preferably between 100 and 300 nucleotides but longer polynucleotides, up to 1500 nucleotides, can be considered. The term "primer" as used herein refers to an oligonucleotide either naturally occurring (e.g. as a restriction fragment) or produced synthetically, which is capable of acting as a point of initiation of synthesis of a primer extension product, which is complementary to a part of a nucleic acid strand (template or target sequence) when placed under suitable conditions (e.g. buffer, salt, temperature and pH) in the presence of nucleotides and an agent for nucleic acid polymerization, such as an enzyme, for instance DNA dependent or RNA dependent polymerase. Normally a set of primers will consist of at least two primers, one "upstream" primer and one "downstream" primer, which together define the amplicon (the sequence that will be amplified using said primers and that is a part of or complementary to a part of the target sequence). One of the primers hybridises to the (+) strand, while the second one hybridises to the (−) strand of the target. The length of the primer should be between 10 and 50, preferably between 15 and 30 nucleotides. A primer could additionally be associated to a promoter sequence for instance a T7 promoter.

As used herein the term "probe" is intended to comprise a stretch of nucleotides hybridising to the amplicon. Preferably the hybridising part is a stretch of 10-50, more preferably 15-35, most preferably 15-30 nucleotides. The probe according to the invention is preferably a so-called molecular beacon (MB). A class of oligonucleotide probes, referred to as molecular beacons, that facilitate homogeneous detection of specific nucleic acid target sequences has been described (Piatek et al. (1998) Nature Biotechnology 16:359-363; Tyagi and Kramer (1996) Nature Biotechnology 14:303-308). Molecular beacons are single-stranded oligonucleotides having a stem-loop structure. The loop portion contains the sequence complementary to the amplicon (either DNA or RNA). The stem is formed due to hybridisation of the complementary sequence of the 3'-end with the 5'-end. The stem can be unrelated to the amplicon and is double-stranded. One arm of the stem is labelled with a fluorescent dye (fluorophore) at its freed end, whereas the other one is coupled to a quenching moiety also at its freed end. In the stem-loop state the probe produces only little fluorescence because the energy of the fluorophore is transferred to the quenching molecule. When the molecular beacon hybridises to the amplicon the stem-loop structure is lost and the quencher and fluorophore become separated. At that stage the fluorescence emitted by the fluorophore is no longer quenched and can be detected and quantified.

The present invention will be further illustrated in the Examples that follow and which are not intended to limit the invention in any way.

BRIEF DESCRIPTION OF THE FIGURES

FIG. 1: IC (internal control is used as target) at 41° C.

FIG. 2: IC at 65° C.

Lines are as indicated in the legend. Closed symbols are from samples that were heated two times to 65° C. Open symbols are from samples that were not heated to 65° C.

The chronology of these experiments is the following: 0-60 minutes (not shown): the NASBA amplification.

60-70 minutes: 10 minutes heating to 65° C. to stop the NASBA.

It is not possible to measure fluorescence during this heating step.

70-80 minutes: 10 minutes measurement of fluorescence to know the starting level of fluorescence before RNA degradation.

80-90 minutes: Addition of the mixture of RNase A and PRI. This took approximately 10 minutes to fill all wells.

90-135 minutes: 45 minutes measurement of fluorescence to see whether RNA was degraded by the mixture. Note: No degradation (flat line) means Rnase A inhibition by PRI. This is only observed when 2 U/μl PRI is added.

135-145 minutes: 10 minutes heating to inactivate PRI.

145-160 minutes: measurement of fluorescence to see whether RNA was degraded.

160-170 minutes: 10 minutes heating to inactivate PRI.

170-185 minutes: measurement of fluorescence.

Figure 7:
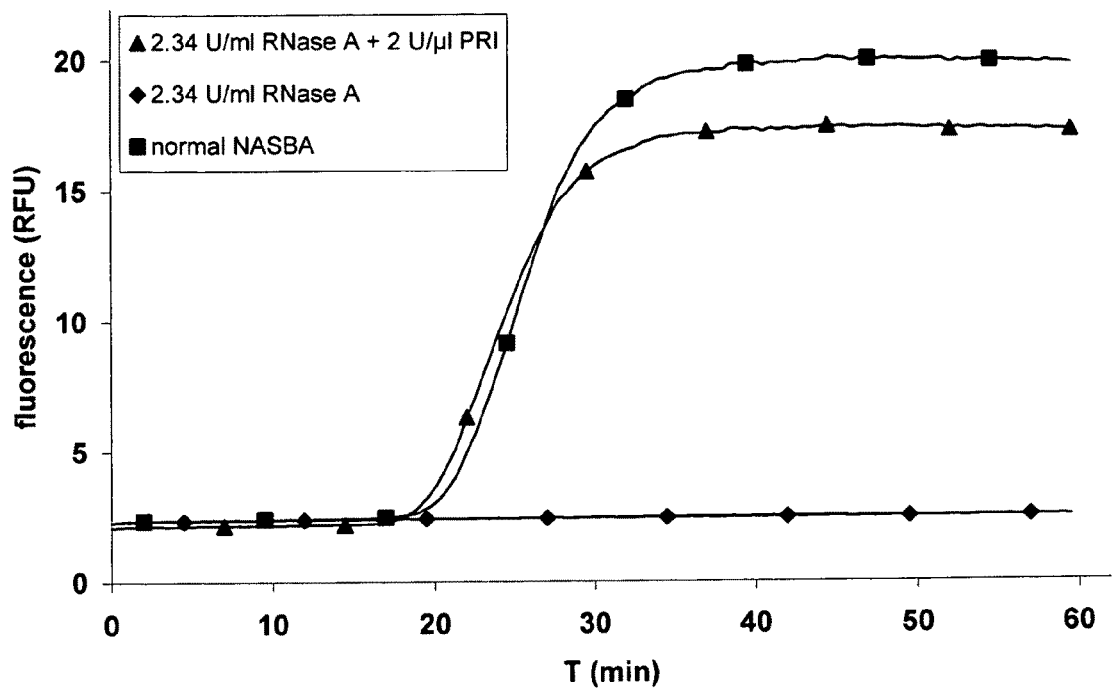

FIG. 7: Influence of RNase A and ribonuclease inhibitor on course of NASBA.

NASBA curves (IC-signal, average of a measurement in threefold): normal; in the presence of RNase A; in the presence of RNase A and PRI.

Figure 8:
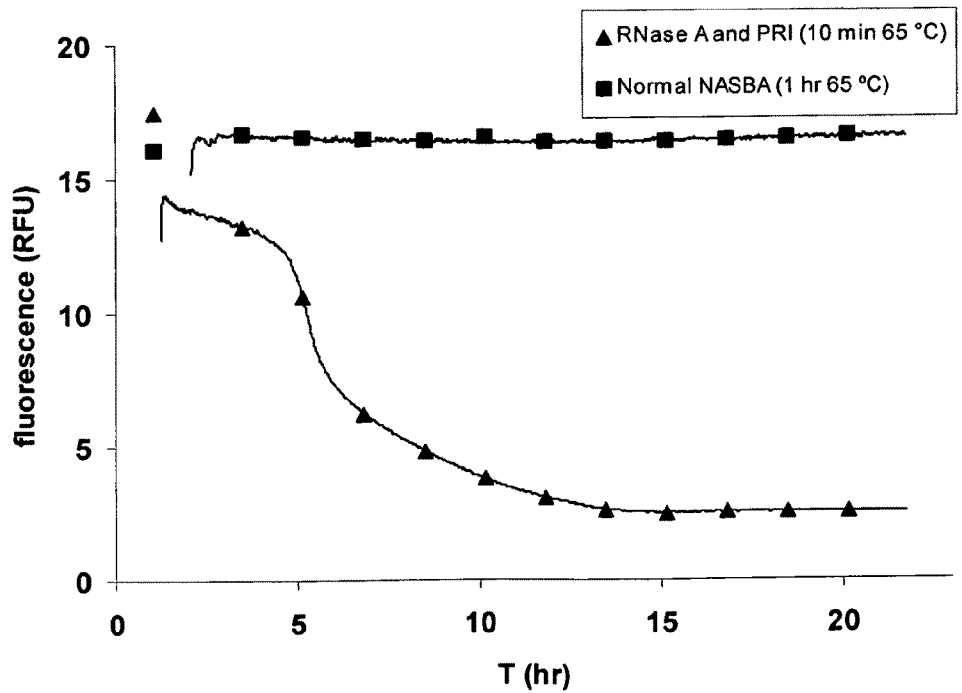

FIG. 8: Inactivation of PRI and Activation of RNase A after NASBA amplification and heating. Fluorescence was not measured during the heating. The line of the normal NASBA is an average of four measurements, while the lines of the NASBAs performed in the presence of RNase A and PRI are averages of eight measurements.

Figure 9:
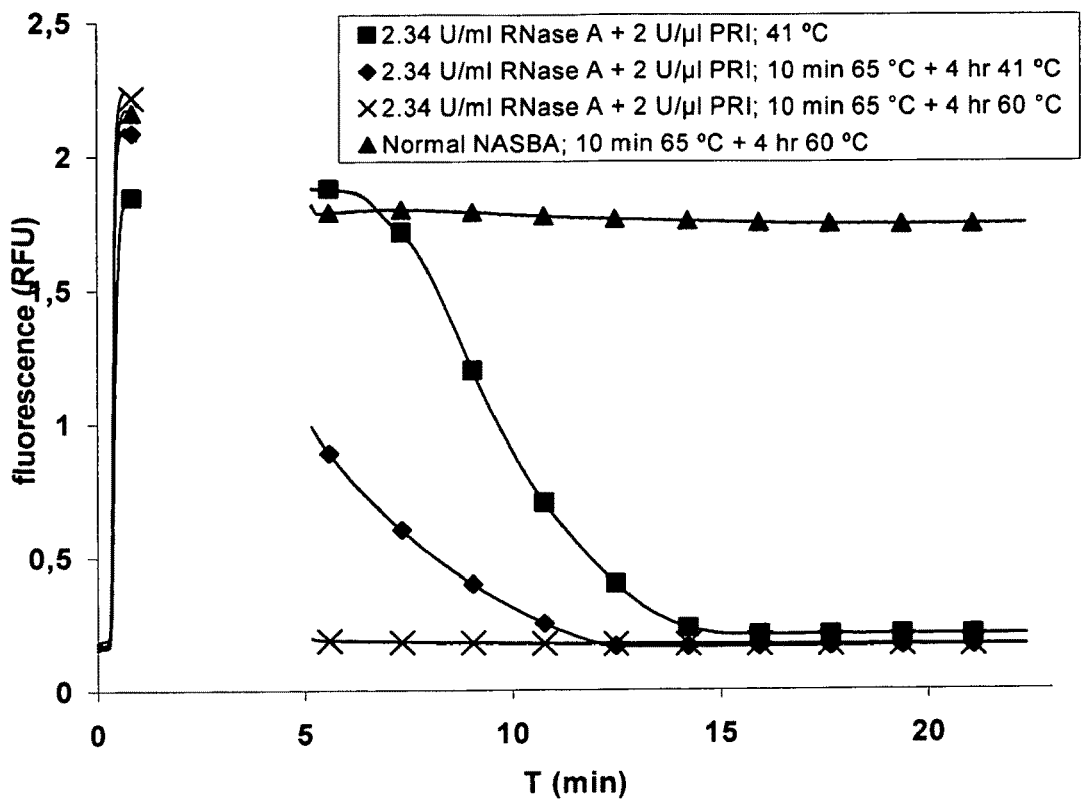

FIG. 9: Optimization of RNA degradation.

Figure 10:
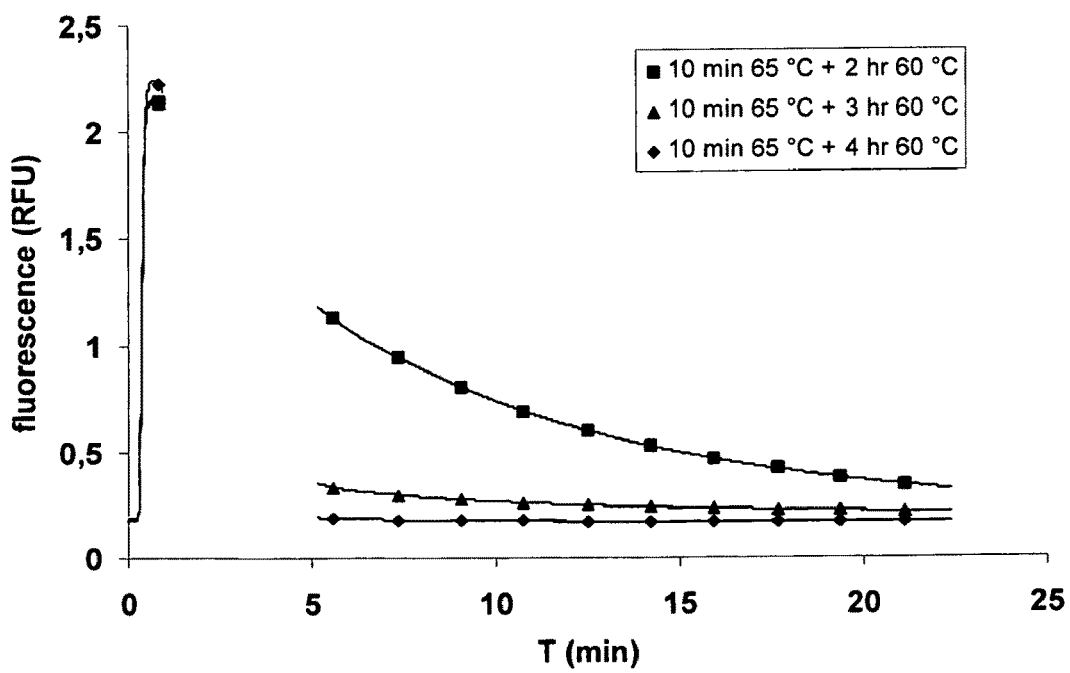

FIG. 10: RNA degradation at 60° C.

The following examples are based on HIV NASBA amplification. Unless stated otherwise, all HIV amplifications were performed as described in example 1. The results below exposed could be derived for the other biological targets, such as other virus (HCV, HPV, etc.), bacteria (listeria, mycobacteria), fungi, yeast . . .

EXAMPLE 1

Determination of Suitable Conditions

Experiments were performed to investigate the suitable conditions to degrade the RNA after a NASBA reaction:
- terminate the NASBA reaction;
- determine suitable concentrations of RNase A and ribonuclease inhibitor;
- determine a suitable temperature to activate RNase A and inactivate ribonuclease inhibitor.

Methods

Enzyme accuspheres (NucliSENS EasyQ Basic Kit bioMérieux, Ref. 280104, Boxtel (NL)) were dissolved in enzyme diluent (purified water class 1, buffered with trisaminomethane to pH 8.5) to prepare an enzyme solution. 45 µL enzyme diluent was used for every enzyme accusphere. Primer/beacon accuspheres (NucliSENS EasyQ HIV-1 v1.2 bioMérieux, Ref. 285036, Boxtel (NL)) were dissolved in primer diluent (80 mM tris(hydroxymethyl)aminomethane, 33% dimethylsulfoxide, 139 mM KCl, pH 8.5) to prepare a primer/beacon solution (concentration in primer/beacon solution: 0.4 µM of both primers (HIV-1 GAG-1), 0.2 µM of both molecular beacons (2'-O-Me beacon WT HIV 1 and beacon Q HIV-1), 24 mM $MgCl_2$, 140 mM KCl, 10 mM dithiothreitol, 2 mM dATP, 2 mM dCTP, 2 mM dGTP, 2 mM DTTP, 4 mM rATP, 4 mM rCTP, 4 mM rUTP, 3 mM rGTP and 1 mM rITP). 90 µL primer diluent was used for every accusphere. Synthesized RNA template was used as sample. The sample was prepared by dissolving one RNA accusphere in 1,000 µL NASBA-water and adding 20 µL of this solution to 980 µL NASBA-water. The used template accuspheres contained IC-RNA ($1.2 \times 10^6$ templates/accusphere, resulting in 120 templates per test). As negative control, water was used as sample.

The IC-RNA is similar to WT-RNA, but the sequence to which the molecular beacons bind is different. Consequently, IC-RNA is used as a model system. 5.0 µL of sample was put in a well of a PCR strip (PCR Strip Tubes 1×8, 0.2 ml, CLR 0.2 mL WITHOUT CAP, Greiner bio-one, art. 673210) and 10.0 µL of the prepared primer/beacon solution was added. 5.0 µL of the prepared enzyme solution was put in each cap of a cap-strip (PCR Strip Caps, 1×8, Dormed Lid, for 0.2 ml Strip Tubes, Greiner bio-one, art. 373270). The wells were placed in a Nuclisens EasyQ Incubator (Molecular Diagnostic, bioMérieux, Ref. 285204, Boxtel (NL)) in which they were kept for 2 minutes at 65° C. and afterwards for 2 minutes at 41° C., while a plate was placed on them to minimize evaporation of the solvent. The caps were put on the wells and they were mixed by turning them two times upside down. Wells were immediately transferred to the Nuclisens EasyQ Analyzer (Molecular Diagnostic, Ref. 285060, bioMérieux, France) in which fluorescence was measured for 1 hour at 41° C. using Director 2.0 software (Molecular Diagnostic, Ref. 271440, bioMérieux, France). Fluorescence of molecular beacons was measured. The excitation wavelength of the one that hybridizes was 578 nm and its emission was measured at 604 nm.

1-1 Terminating the NASBA reaction

Goal

From previous experiments (data not shown) it is known that the NASBA reaction is not always completed after 60 minutes. This invention relates to RNA degradation. RNA formation after a NASBA amplification can be detrimental for that purpose.

Method

Sixteen NASBA HIV amplifications were carried out in the wells of a PCR strip with RNA accuspheres containing IC-RNA, but stopped after 20 minutes. One strip containing eight NASBAs was placed for 10 minutes at 65° C., while a control was left at 41° C. Afterwards, fluorescence was measured at 41° C. for 1 hour.

Results

Figure 1:
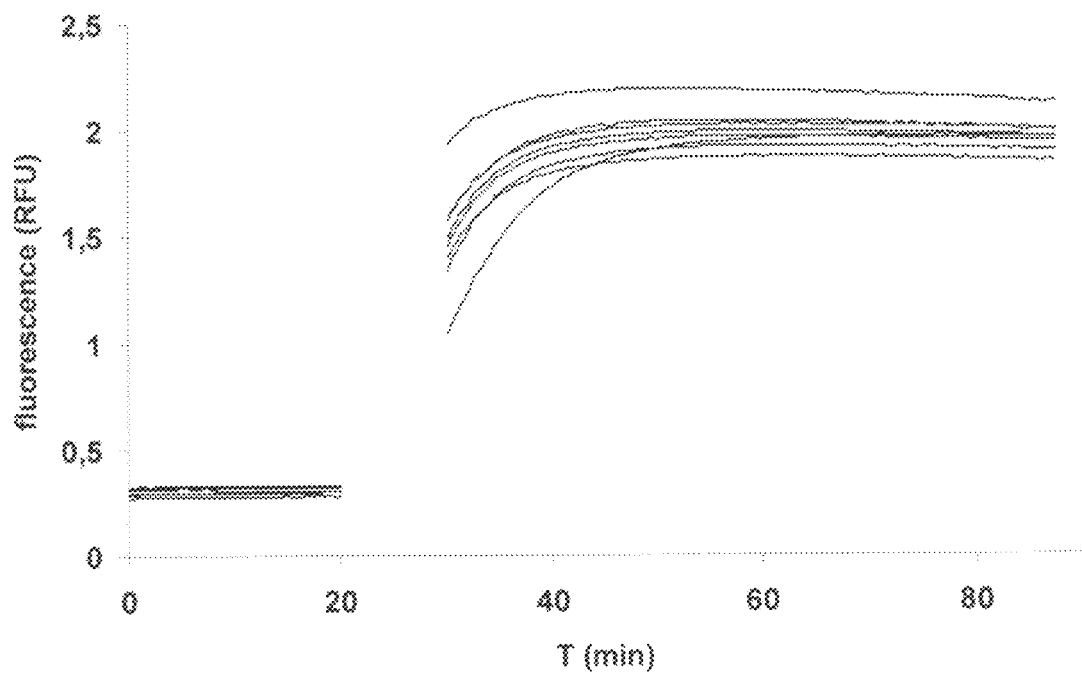
FIGS. 1 and 2: Terminating the NASBA reaction. Fluorescence in the NASBA solutions after heating in absence of RNase A and ribonuclease inhibitor (Relative Fluorescence Unit per minute).
Figure 2:
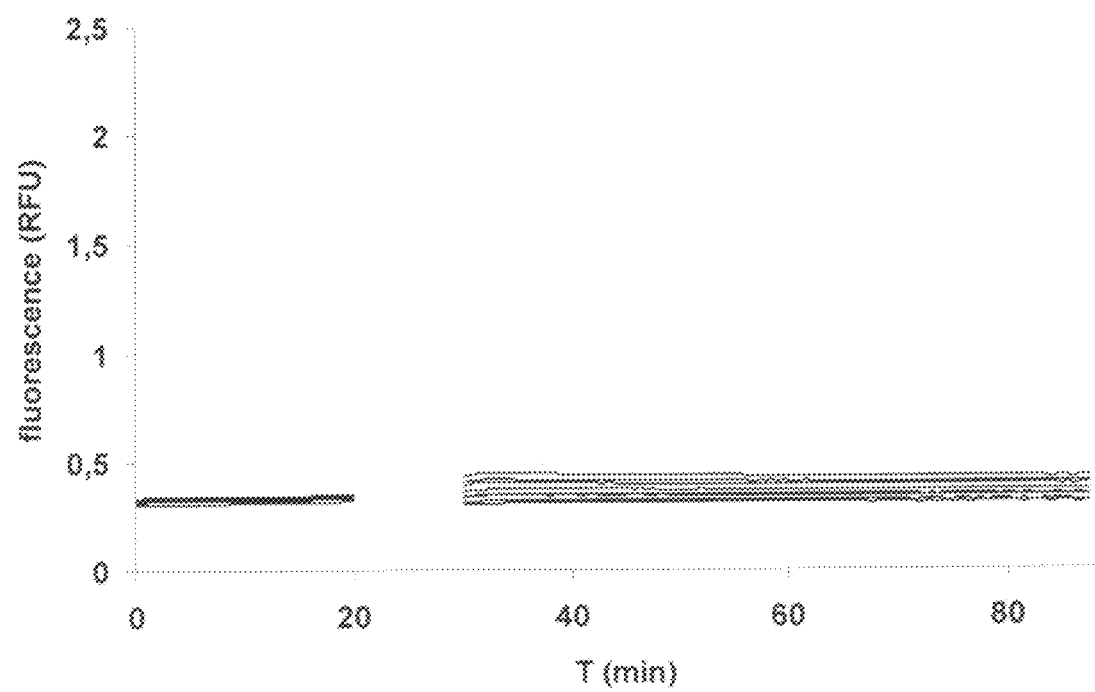

NASBAs were carried out, but after 20 minutes the NASBA enzymes were inactivated by leaving NASBA solutions for 10 minutes at 65° C. (FIG. 2). Control NASBAs were left at 41° C. (FIG. 1). Fluorescence was measured at 41° C. for 1 hour after the heating step (FIGS. 1 to 2).

After the heating step, no increase in fluorescence of any of the beacons is observed for the NASBA solution that had stood at 65° C. The other solution, which had stood at 41° C., shows an increase in fluorescence for all IC, which is normal for a NASBA that is performed with these amounts of template RNA. This means that 10 minutes heating at 65° C. stops the NASBA and no more RNA is formed.

1-2 RNA Digestion by RNase A

Goal

Experiments were performed to investigate whether RNase A can be used to degrade RNA after a NASBA and what concentration of it is suitable. NASBAs were carried out in wells of PCR strips and after the assay, RNase A was added at different concentrations. The solutions were heated for 10 minutes at 65° C. and RNA degradation was monitored afterwards at 41° C. by measuring the fluorescence of the molecular beacons that were already present.

Method

Solutions of RNase I "A" (Amersham, art nr 27-0323-01, 936 U/mg) at different concentrations (0, 425, 1265, 3840, 11700, 34500, 105000, 315000 and 935000 U/l) were prepared. Twenty seven NASBA reactions were performed with RNA accuspheres containing only IC-RNA as template. A 5 µl volume of the different RNase A solutions was added at the end of the NASBA. This was done three times for every produced RNase I "A". The solutions were heated for 10 minutes to 65° C. to stop the NASBA reaction. Afterwards fluorescence was measured at 41° C.

Results

Figure 3:
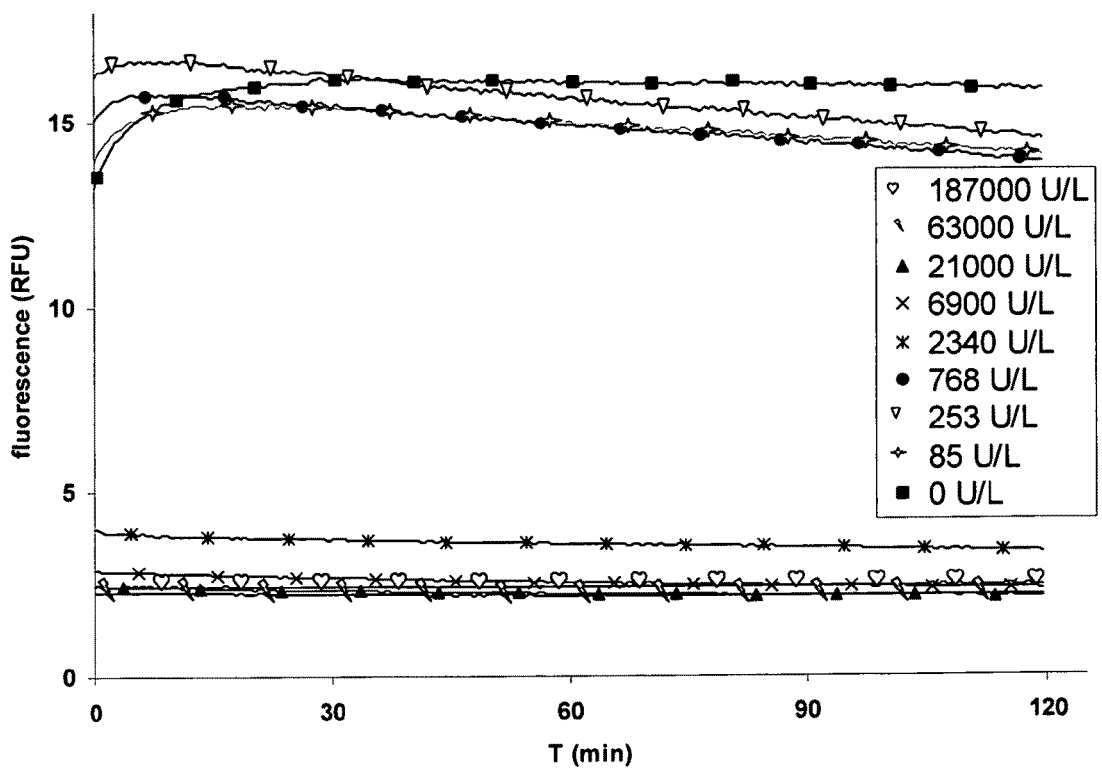
FIG. 3: RNA digestion by RNase A. Fluorescence in the NASBA solution after addition of RNase A.

Addition of RNase A to a NASBA solution after the NASBA assay but before the amplification reaction has been stopped by heating for 10 minutes at 65° C. leads to a decrease in fluorescence of the beacons (FIG. 3), which indicates that amplicons are degraded by the RNase A. The decrease in fluorescence was not observed when water was added instead of RNase A (0 U/L concentration).

When RNase A is added to reach a concentration of RNase A in the NASBA solution of 2340 U/L or more, RNA is rapidly degraded. When the amount of RNase A is lower, the rate of degradation becomes lower (compare different lines in the figure).

1-3 RNAse A Inhibition by Ribonuclease Inhibitor
Goal

RNase A can be used to break down RNA after a NASBA reaction. In this experiment the feasibility of ribonuclease inhibitor, PRI, to inhibit RNase A is shown.

Method

Figure 4:
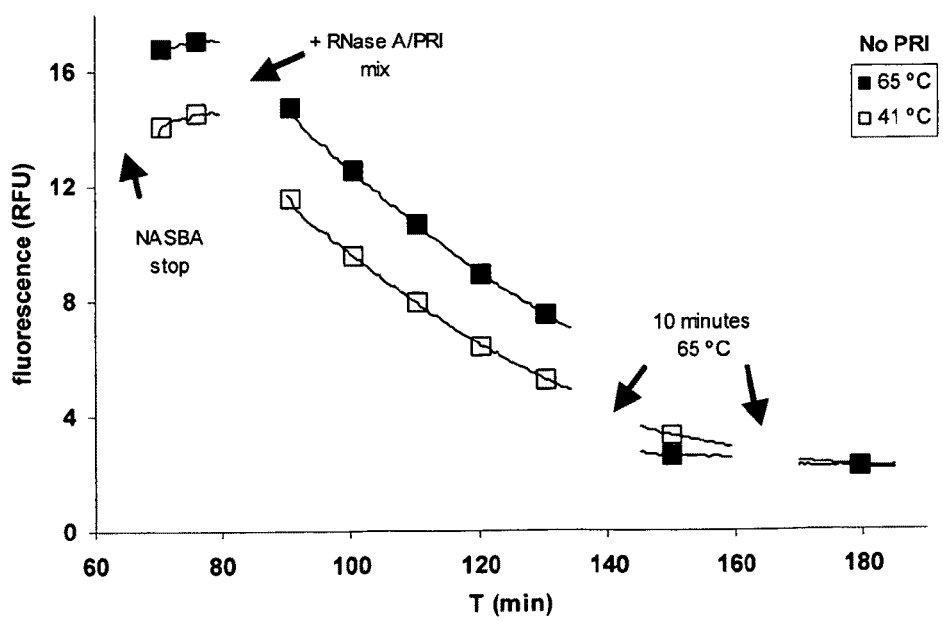
FIG. 4-6: RNAse A inhibition by ribonuclease inhibitor. Fluorescence in the NASBA solution after amplification and after addition of RNase A (2.34 U/mL) and PRI (0, 1 or 2 U/μL for FIGS. 4, 5, 6 respectively).
Figure 5:
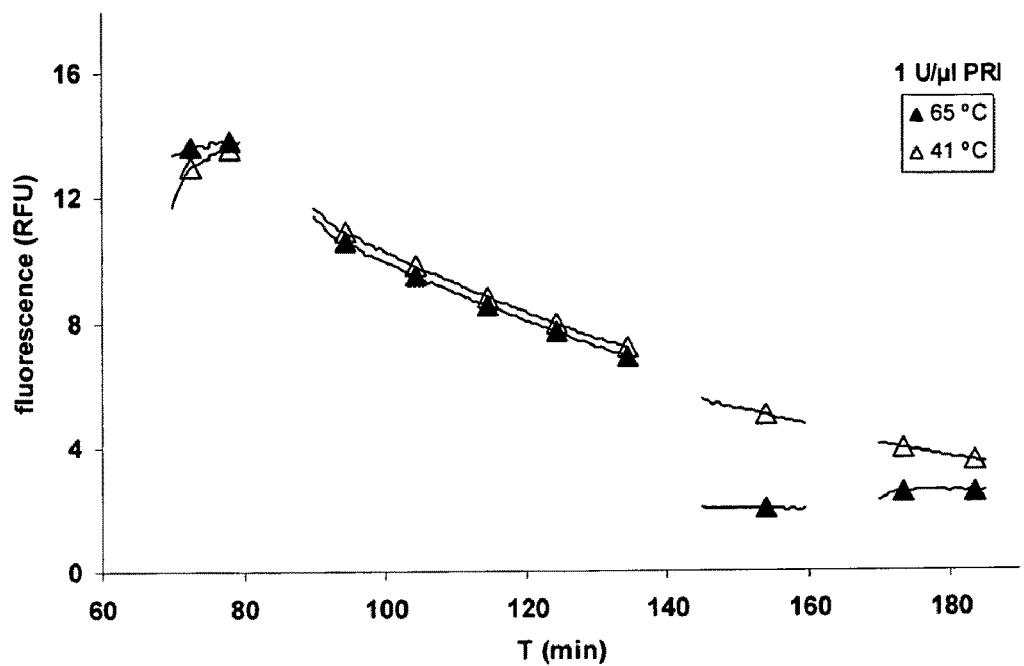
Figure 6:
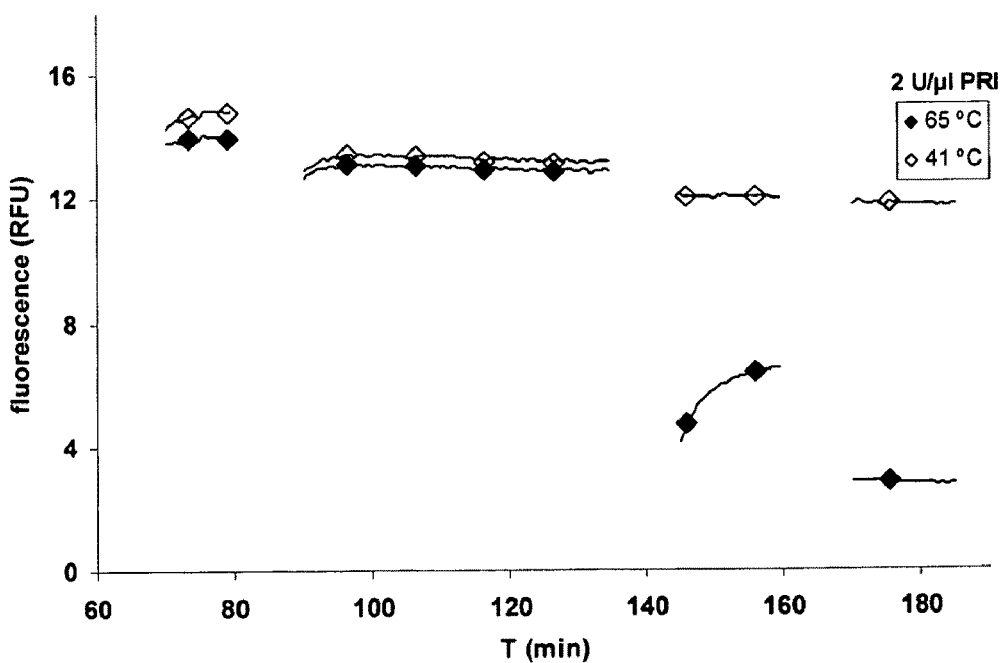

Solutions containing both 11.7 U/mL RNase I "A" and 0, 5 or 10 U/µl PRI were prepared. Six NASBA reactions were carried out with IC-RNA accuspheres as template. After one hour, the NASBA reactions were stopped by putting the solutions at 65° C. for 10 minutes. The NASBA-wells were opened and to each well 5 µL of one of the prepared solutions containing RNase A and PRI was added. Every solution was added twice: one was heated to inactivate PRI, one was left at 41° C. as a control. This resulted in NASBA-solutions containing 2.34 U/mL RNase A and 0, 1 or 2 U/µL PRI (FIGS. 4, 5, 6 respectively). Fluorescence was measured for 45 minutes at 41° C. to allow RNase A to break down the RNA whenever inhibition by PRI was not sufficient. Afterwards, samples were placed two times at 65° C. for 10 minutes to deactivate the PRI, while their controls were left at 41° C. Fluorescence was measured in between and afterwards for 15 minutes at 41° C. to visualize RNA degradation.

Results (FIGS. 4-6)

The inhibitory effect of PRI on 2.34 U/mL RNase A is already observed at a concentration of PRI of 1 U/µL (FIG. 5). When more PRI is present, the inhibition is enhanced. The horizontal line in FIG. 6 of the sample that contained 2 U/µl indicates that no RNase A activity was present after addition of PRI at that concentration.

RNA degradation is induced or accelerated when the samples were left for 10 minutes at 65° C. Degradation was even accelerated for the sample that did not contain any PRI. The increase in reaction rate is, in that case, caused by an increase in activity of RNase A at higher temperature. It is known from literature that the optimum temperature for RNA cleavage by RNase A is 60° C. For samples that did contain PRI, the accelerated RNA cleavage is mainly caused by the inactivation of PRI during the heating for 10 minutes at 65° C.

EXAMPLE 2

Influence of RNase A and Ribonuclease Inhibitor on Course of NASBA Reaction

Goal

In this experiment RNase A and PRI were added to a NASBA reaction prior to the start of the amplification. The influence of these enzymes on the course of the NASBA is investigated.

Method

NASBA reactions with IC-RNA accuspheres as template were performed in the presence and absence of RNase A and PRI and in the presence of only RNase A. These proteins were added to the enzyme diluent prior to dissolution of the enzyme accusphere. For the NASBA amplification realized in presence of both RNase A and PRI, the enzyme diluent was prepared by adding 11.2 µL RNAguard to 9 µL 46.8 U/mL RNase I "A" and 24.8 µL enzyme diluent and contained 9.36 U/ml RNase A and 10 U/µL PRI. For the reaction with the sole presence of RNase A, the enzyme diluent was prepared by adding 9 µl 46.8/mL RNase I "A" to 36 µl enzyme diluent and contained 9.36 U/ml RNase A. NASBAs were performed in threefold for all 3 conditions.

Results

NASBA assays in the presence of 2.34 U/mL of Rnase A and 120 copies of IC-RNA as template do not show an increase in fluorescence during the test (FIG. 7). The IC-curve proceeds like a normal IC-curve for a NASBA when 2 U/µL PRI is added besides 2.34 U/mL RNase A. It is not possible to carry out a NASBA reaction when the concentration of RNase A in the solution is 2.34 U/ml. However, this becomes possible when besides RNase A, PRI is added at a concentration of 2 U/µl. PRI inhibits RNase A in such a way that a NASBA amplification can be carried out in the presence of both proteins.

EXAMPLE 3

Inactivation of Ribonuclease Inhibitor and Activation of RNase 3-1 Inactivation of PRI
Goal Investigate whether it is possible to induce RNA degradation after a NASBA reaction by heat-inactivation of PRI.

Method

Eight HIV-NASBAs were carried out in the presence of RNase A and PRI with RNA accuspheres containing IC-RNA. Therefore, the enzyme diluent was replaced by a mixture of 24.8 µl enzyme diluent, 9 µl 46.8 U/ml RNase I "A" and 11.2 µl RNAguard. Fluorescence was measured for 10 minutes directly after the NASBA using Ascent software (see the two points at 1 hour of FIG. 8). Thereafter, the wells were put for 10 minutes at 65° C. to inactivate PRI. The wells were put back at 41° C. directly after this temperature treatment and fluorescence was measured for over 20 hours using Ascent software. The negative control was measured in fourfold and was a normal NASBA, which was left for 1 hour at 65° C. after the test.

Results

RNase A was activated after the NASBA by leaving the solution for 10 minutes at 65° C. It starts at 1 hour and 20 minutes (1 hour NASBA+10 minutes measurement of fluorescence+10 minutes inactivation of PRI). At that temperature PRI irreversibly loses its ability to inhibit RNase A. It was already shown that the NASBA reaction is stopped after leaving the solution for 10 minutes at 65° C. and that no more RNA is formed. From the NASBA-curves only the end values are shown in FIG. 8. It is useless to measure fluorescence during the heating step because the high temperature causes all beacons to dissociate from their target and no conclusion can be drawn from the measured signal.

Heating a normal NASBA for 1 hour at 65° C. does not lead to a decrease in fluorescence of the beacon. Unlike for a normal NASBA, heating a NASBA that was carried out in the presence of RNase A and PRI for 10 minutes to 65° C. leads to a decrease in fluorescence, which indicates that target RNA is broken down by the RNase A.

3-2 Optimization of RNA Degradation
Goal

This experiment aims to reduce the time that is necessary for RNase A to degrade RNA to below the level of detection of the molecular beacons Method Sixteen NASBAs were carried out with IC-RNA accuspheres as template. four of them were a normal NASBA and twelve were with the addition of RNase A and PRI. For those that were carried out with RNase A and PRI, the enzyme diluent was replaced by a mixture of 24.8 µl enzyme diluent, 9 µl 46.8 U/ml RNase I "A" and 11.2 µl RNAguard. Four samples that contained RNase A and PRI were left at 41° C. after the test. The other samples were placed for 10 minutes at 65° C. after the NASBA. Afterwards, the normal NASBAs and four of the NASBAs with RNase A and PRI were placed for 4 hours at 60° C. The remaining four NASBAs were placed for 4 hours at 41° C. All samples were put back in the analyzer at 41° C. immediately after these temperature treatments. Back in the analyzer, fluorescence was measured using director software.

Results

The rate of RNA degradation after the NASBA was increased by changing the temperature after the PRI inactivation step to 60° C. (FIG. 9). It is remarkable that RNA degradation also takes place when the PRI is not heat-inactivated, although this process starts later. This means that the PRI can be inactivated even at 41° C.

3-3 Improvement to the RNA Degradation at 60° C.

Goal

Investigate whether the duration of the heating step after the inactivation of PRI can be shortened.

Method

Twelve NASBAs in the presence of RNase A and PRI were performed with IC-RNA accuspheres as template. At the end of the test they were heated for 10 minutes at 65° C. and divided into three groups of four. The groups were put for 2, 3 or 4 hours at 60° C. After the heating all samples were put back in the analyzer at 41° C. and fluorescence was measured using director software.

Results

Only a small amount of RNA was degraded after standing for 2 hours at 60° C. (■ in FIG. 10). More RNAs are degraded when the period at 60° C. is prolonged to 3 hours (▲), but the degradation is not sufficient to reach the lower detection limit of the molecular beacons. Again, this was achieved when the solution is left for 4 hours at 60° C. (♦).

CONCLUSION

This research focused on the prevention of RNA contamination after a NASBA reaction. It was shown that the combination of RNase A and ribonuclease inhibitor forms a promising solution to lower the risk of RNA-contamination after a NASBA reaction. It is possible to carry out a NASBA reaction in the presence of RNase A and PRI and RNA cleavage can be induced by a single heating step afterwards without opening the reaction vessel. After the initial activation step, which takes 10 minutes, it takes 4 hours at 60° C. to break down the RNA to below the detection limit of the molecular beacons present in a typical NASBA. All these experiments were performed with an Rnase A concentration of 2.34 U/ml, which is the lowest concentration to achieve a good RNA degradation after a typical NASBA. By increasing this concentration, as well as the one of the ribonuclease inhibitor, it is possible to improve these results (data not shown). Over $10^{12}$ copies of RNA are present at the end of a NASBA and within 4 hours this amount is reduced to less than $10^9$ copies.

It is desirable to stop the RNA amplification at the end of a test to enable RNA degradation without simultaneous RNA production. This can be done by heating the NASBA for 10 minutes to 65° C. Although heating to a lower temperature may be sufficient to stop the NASBA, heating for 10 minutes to 65° C. is preferred because PRI is inactivated during this temperature treatment. Heating a NASBA reaction that was carried out in the presence of RNase A and PRI for 10 minutes to 65° C. stops the RNA production and can simultaneously start RNA degradation by RNase A.

RNAs are rapidly degraded after a NASBA amplification when RNase A is added to a final concentration of 2.34 U/mL. RNA cleavage by RNase A at that concentration is inhibited when PRI is added to a concentration of at least 2 U/μL. These proteins can be added to a HIV-NASBA test at these concentrations without causing a change in the course of the NASBA-curves and without affecting the test result. RNA degradation was also observed for samples that were left at 41° C. In that case it took over 6 hours before RNA degradation was observed. PRI is an unstable enzyme and is probably slowly inactivated at 41° C., causing a slow but steady increase in RNase A activity. After the initial activation, RNA degradation is fastest when the cleavage takes place at 60° C., which is the optimum temperature for RNA cleavage by RNase A.

The invention claimed is:

1. A method for treating a solution containing at least one target nucleic acid of interest to be amplified comprising the following steps:
    contacting suitable amplification reagents and at least one target nucleic acid in the presence of
        at least one ribonuclease enzyme (RNase), and
        at least one ribonuclease inhibitor;
    the RNase being inhibited by the ribonuclease inhibitor;
    forming a solution of the amplification reagents, the RNase, the ribonuclease inhibitor and the target nucleic acid;
    performing a transcription-based amplification of the target;
    treating said solution in order to inactivate the ribonuclease inhibitor and activate the RNase; and
    degrading any RNA that is present in the solution by the action of said RNase.

2. A method according to claim 1, wherein the RNase and the ribonuclease inhibitor are mixed before being brought into contact with the suitable amplification reagents and the at least one target nucleic acid.

3. A method according to claim 1, wherein the target nucleic acid is DNA or RNA, in the form of double-stranded nucleic acid or single-stranded nucleic acid or a heteroduplex DNA:RNA.

4. A method according to claim 1, wherein after having performed the transcription-based amplification, a detection step is performed.

5. A method according to claim 4, wherein the amplification reagents contain at least one probe to enable the detection step.

6. A method according to claim 1, wherein during performing the transcription-based amplification, a detection step is performed.

7. A method according to claim 6, wherein the amplification reagents contain at least one real-time detection probe to enable the detection step.

8. A method according to claim 1, wherein the treatment is performed in a reaction vessel, and
    before performing the amplification step, the reaction vessel is closed.

9. A method according to claim 1, wherein the RNase is RNase A, RNase B and/or RNase C.

10. A method according to claim 1, wherein the ribonuclease inhibitor inhibits the RNase present in the solution but not enzymes suitable for amplification.

11. A method according to claim 1, wherein the ribonuclease inhibitor is placental ribonuclease inhibitor or porcine ribonuclease inhibitor (PRI).

12. A method according to claim 1, wherein the treating step comprises heating that occurs between 41° C. and 100° C.

13. A method according to claim 12, wherein the heating step is a one step process.

14. A method according to claim 12, wherein the heating step is a two step process:
- a first heating step where the temperature is higher than the second step to inactivate the ribonuclease inhibitor and activate the RNase;
- a second heating step where the temperature is lower than the first step in order to increase the rate of RNA degradation.

15. A method according to claim 14, wherein the temperature of the first heating step is between 60° C. and 75° C.

16. A method according to claim 14, wherein the temperature of the second heating step is between 30° C. and 70° C.

17. A method according to claim 14, wherein the first heating step stops RNA amplification.

18. A method according to claim 14, wherein the temperature of the first heating step denatures an RNA polymerase and a reverse transcriptase, and the temperature of the second heating step increases the rate of degradation of single stranded RNA and RNA in an RNA:DNA complex by respectively RNase A and RNase H.

19. A method according to claim 12, wherein the heating step is a cyclic process.

20. A method according to claim 19, wherein the cyclic process consists of a heating step to render RNA single stranded and a heating step to degrade RNA.

21. A method according to claim 19, wherein the cyclic process takes place after inactivation of the ribonuclease inhibitor.

22. A method according to claim 1, wherein the amplification reaction is a NASBA reaction.

23. A method according to claim 1, wherein the reagents contain at least one probe, which is a molecular beacon.

24. A method of degrading RNA when present in a solution, comprising:
- amplifying a target nucleic acid of interest when present in a solution, the solution comprising nucleic acids, amplification reagents, an RNase, and an RNase inhibitor;
- inactivating the RNase inhibitor in the solution; and
- degrading RNA, when present in the solution, with the RNase after inactivating the RNase inhibitor.

25. A method according to claim 24, wherein the RNase inhibitor is inactivated by heating.

26. A method according to claim 24, wherein the RNase inhibitor is inactivated at a temperature of at least 41° C.

27. A method according to claim 24, wherein the RNase inhibitor is inactivated by heating the solution at a first temperature, and the rate of RNA degradation is increased by heating at a second temperature that is lower than the first temperature.

* * * * *